United States Patent [19]

Saari

[11] Patent Number: 4,935,443
[45] Date of Patent: Jun. 19, 1990

[54] N-SUBSTITUTED-3-NITRO-4-(UREIDOOX-YMETHYL)-BENZENESULFONAMIDES AS RADIATION ENHANCERS

[75] Inventor: Walfred S. Saari, Lansdale, Pa.

[73] Assignee: Merck & Co., Inc., Rahway, N.J.

[21] Appl. No.: 371,151

[22] Filed: Jun. 26, 1989

[51] Int. Cl.$^5$ ................. C07C 83/10; A61K 31/21
[52] U.S. Cl. ................................. 514/507; 560/313
[58] Field of Search ...................... 560/313; 514/507

[56] References Cited

U.S. PATENT DOCUMENTS

| 4,603,133 | 7/1986 | Engelhardt et al. | 560/313 |
|---|---|---|---|
| 4,647,588 | 3/1987 | Engelhardt et al. | 560/313 |
| 4,654,369 | 3/1987 | Saari | 560/313 |
| 4,694,020 | 9/1987 | Engelhardt et al. | 560/313 |
| 4,731,369 | 3/1988 | Engelhardt et al. | 560/313 |

OTHER PUBLICATIONS

Halliwell et al., Free Radicals in Biology and Medicine, Oxford, pp. 238–241 (1985).
Collins, A., Int. J. Radiat. Biol., vol. 51, No. 6, 971–983, (1987).

Primary Examiner—Mary C. Lee
Assistant Examiner—Robert C. Whittenbaugh
Attorney, Agent, or Firm—Richard S. Parr; Michael C. Sudol

[57] ABSTRACT

Disclosed are compounds having the formula:

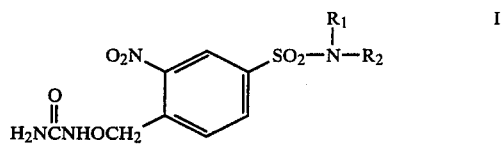

wherein:
$R_1$ is hydrogen, analkyl group having 1 to 6 carbon atoms, an alkyl group having 1 to 6 carbon atoms in which one or more of the carbon atoms are substituted with a hydroxy group;
$R_2$ is an alkyl group having 1 to 6 carbon atoms in which one or more of the carbon atoms are substituted with a hydroxy group, an alkyl group having 1 to 6 carbon atoms which contains an amino group in which the amino function is substituted with hydrogen or one or two individual alkyl groups having 1 to 6 carbon atoms;

or a pharmaceutically acceptable salt thereof.

These compounds increase the sensitivity of hypoxic cancer cells to radiation. Methods of preparing such compounds, protocols for administering them to human patients and animals, and pharmaceutical compositions containing them are also disclosed.

5 Claims, No Drawings

N-SUBSTITUTED-3-NITRO-4-(UREIDOOXYMETHYL)-BENZENESULFONAMIDES AS RADIATION ENHANCERS

BACKGROUND OF THE INVENTION

The present invention relates to derivatives of N-substituted-3-nitro-4-(ureidooxymethyl)benzenesulfonamides, used as sensitizers of hypoxic tumor cells to therapeutic radiation.

Radiation is an effective means of treatment for various types of cancers and tumors. However, it has been found that the effectiveness of radiation is decreased if there is an insufficient supply of oxygen (hypoxia) in the area undergoing treatment. In order to achieve the same proportion of hypoxic tumor cell kill, about three times the radiation dose is required for well-oxygenated cells. Various approaches have been tried to solve this problem including increased oxygen exposure with radiation treatment and the use of drugs that will make hypoxic tumor cells more sensitive to radiation. Halliwell, B. et al., *Free Radicals in Biology and Medicine*, Oxford, 238–241 (1985). Some drugs which make hypoxic tumor cells more sensitive to radiation operate by inhibiting the production of DNA precursors. Examples of such inhibitors are deoxyadenosine and hydroxyurea. These compounds potentiate chromosome damage initiated by ionizing radiation in mammalian cells. This potentiation most likely reflects an inhibition of DNA repair. Collins, A., *Int. J. Radiat. Biol.*, Vol. 51, No. 6, 971–983 (1987).

Various types of compounds have been utilized to enhance the effects of radiation on hypoxic tumor cells. U.S. Pat. No. 4,603,133 discloses the use of 2-[N-(morpholinoalkyl)amino-sulfonyl]-6-nitrobenzoic acids in radiation treatment. U.S. Pat. No. 4,654,369 discloses the use of 2-(substituted sulfamyl)-6-nitrobenzoic acids which are useful as adjuncts to radiation therapy.

U.S. Pat. No. 4,647,588 discloses 2-(substituted sulfamyl) derivatives of 6-nitrobenzoic acids as having activity in increasing the sensitivity of hypoxic tumor cells to therapeutic radiation. (see also U.S. Pat. Nos. 4,694,020 and 4,731,369).

SUMMARY OF THE INVENTION

It has now been discovered that derivatives of N-substituted-3-nitro-4-(ureidooxymethyl)-benzene-sulfonamides are useful for increasing the therapeutic effects of radiation by sensitizing hypoxic tumor cells to radiation therapy. These compounds are selectively toxic to tumor hypoxic cells by the intracellular release of hydroxyurea, a DNA synthesis and repair inhibitor. Thus, it is an object of this invention to provide compounds useful for sensitizing hypoxic tumor cells to radiation. Another object of this invention is to provide methods for synthesizing the compounds of the present invention. Still another object is to provide pharmaceutical compositions containing compounds of the present invention and methods of utilizing the compounds of the invention to enhance the therapeutic effect of radiation. Further objects will become apparent from the disclosure.

DETAILED DESCRIPTION OF THE INVENTION

The compounds of the present invention are of the following formula:

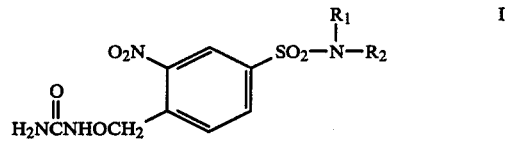

wherein:

$R_1$ is hydrogen, an alkyl group having 1 to 6 carbon atoms, an alkyl group having 1 to 6 carbon atoms in which one or more of the carbon atoms are substituted with a hydroxy group;

$R_2$ is an alkyl group having 1 to 6 carbon atoms in which one or more of the carbon atoms are substituted with a hydroxy group, an alkyl group having 1 to 6 carbon atoms which contains an amino group in which the amino function is substituted with hydrogen or one or two individual alkyl groups having 1 to 6 carbon atoms;

or a pharmaceutically acceptable salt thereof.

Compounds of the invention are electron acceptors which form radical anions in the reducing environment of hypoxic cells or upon irradiation and from which hydroxyurea is released. The $S_{RN}1$ mechanism by which these compounds release hydroxyurea is completely inhibited by molecular oxygen, and offers unique opportunities for the selective release of anions in hypoxic environments.

The $S_{RN}1$ mechanism is a radical chain mechanism which can be initiated by generation of a radical anion. It leads to the nucleophilic substitution of benzylic groups, Y for X in the following sequence:

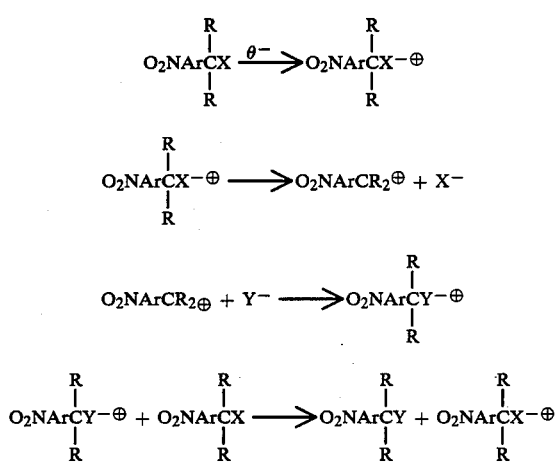

Compounds of the invention are selective radiosensitizers of hypoxic cells. The release of hydroxyurea from the radical anion through an $S_{RN}1$ mechanism takes place under hypoxic conditions.

One preferred compound of the present invention is N-methyl-N-(2-methylaminoethyl)-3-nitro-4-(ureidooxymethyl)-benzenesulfonamide, which has the formula:

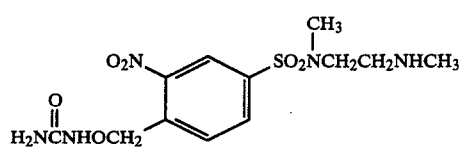

Another preferred compound of the present invention is N,N-Di-(2-hydroxyethyl)-nitro-4-(ureidooxymethyl)-benzenesulfonamide, which has the formula:

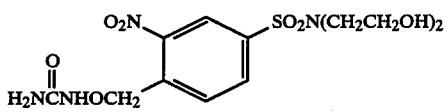

Procedures for synthesis of these compounds are presented in the examples.

The method of treatment of human patients or domestic animals undergoing radiation treatment of malignant disease processes employs the compounds of the present invention in pharmaceutical compositions that are administered orally or intravenously or in depot formulations.

When the compounds are used in conjunction with radiation treatments, the dose employed depends on the radiation protocol for each individual patient. They can be administered from 10 minutes to 5 hours prior to the radiation treatment in a dose of from 0.25 to 4.0 grams per square meter of body surface. The compounds may be employed at intervals during a multi-fraction protocol, and not necessarily with each treatment.

When the compounds are used as cytotoxic agents to hypoxic cells, they can be administered daily in divided doses up to 0.25 to 4.0 grams per square meter of body surface.

The dosage range given is the effective dosage range and the decision as to the exact dosage used must be made by the administering physician based on his judgment of the patient's general physical condition. In determining the dose for the individual patient, the physician may begin with an initial dose of 0.25 g/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

The dosage form for intravenous administration is a sterile isotonic solution of the drug. Oral dosage forms such as tablets, capsules, or elixirs may also be used.

Capsules or tablets containing 25, 50, 100 or 500 mg of drug/capsule or tablets are satisfactory for use in the method of treatment of our invention.

The following examples are intended to illustrate but do not limit the process of preparation, product, compositions, or method of treatment aspects of the invention. Temperatures are in degrees Celsius unless otherwise indicated throughout the application.

EXAMPLE 1

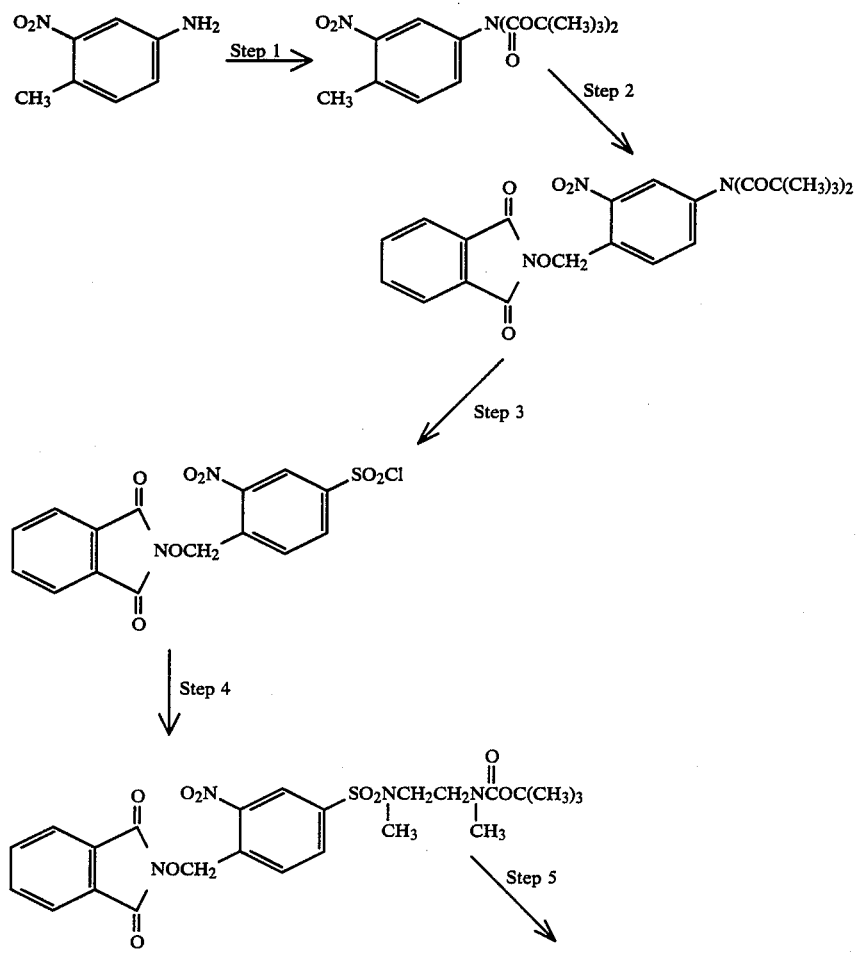

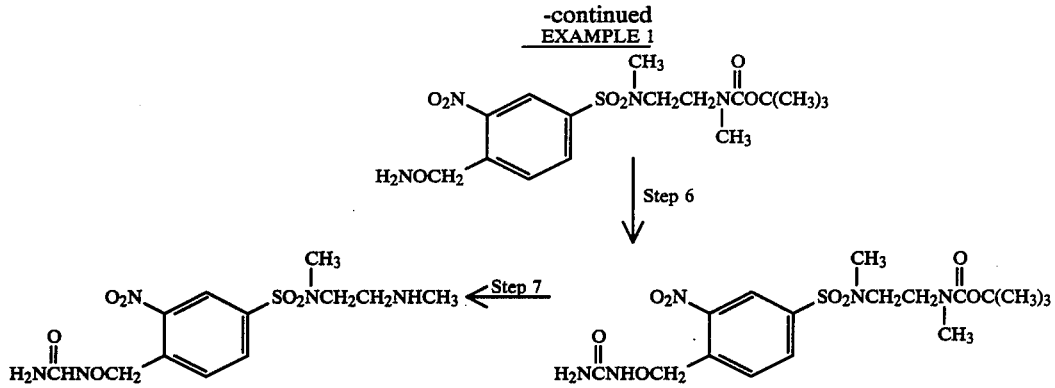

N-METHYL-N-(2-METHYLAMINOETHYL)-3-NITRO-4-(UREIDOOXYMETHYL)-BENZENESULFONAMIDE HYDROCHLORIDE.

Step 1. N,N-Bis(tertbutyloxycarbonyl)-4-methyl-3-nitroaniline.

A solution of ditertbutyl dicarbonate (45.9 g, 0.21 mol) in acetonitrile (75 mL) was added to a stirred solution of 4-methyl-3-nitroaniline (15 g, 0.099 mol) and 4-dimethylaminopyridine (1.2 g, 9.9 mmol) in acetonitrile (150 mL) over 15 minutes and the mixture warmed at 80° minutes until solution was complete. After stirring at room temperature for 18 hours, solvents were removed under reduced pressure and the residue partitioned between EtOAc and 10% citric acid. The organic layer was washed with water, then brine, and dried ($Na_2SO_4$). The filtered solution was concentrated under reduced pressure and the residue flash chromatographed over silica gel. Elution with 1:1 hexane-$CHCl_3$ gave 33.0 g (95%) of product as a yellow oil.

Step 2. N,N-Bis(tertbutyloxycarbonyl)-3-nitro-4-phthalimidooxymethylaniline.

A mixture of N,N-bis(tertbutyloxycarbonyl)-4-methyl-3-nitroaniline (33 g, 93.6 mmol), N-bromosuccinimide (21.4 g, 120 mmol) and dibenzoylperoxide (50 mg) in $CCl_4$ (500 mL) was stirred at reflux under a 100 W bulb for 20 hours. After cooling, succinimide was filtered off and solvents removed under reduced pressure.

This residue, containing 69% bromomethyl derivative, was dissolved in acetonitrile (500 mL), N-hydroxyphthalimide (13.1 g, 80 mmol) and trimethylamine (11.2 mL) added and the solution stirred at reflux for 6 hours under a drierite tube. After concentrating under reduced pressure, the residue was partitioned between EtOAc and water. The water extract was re-extracted two times more with fresh EtOAc and the organic extracts combined. The extracts were washed with brine, dried ($Na_2SO_4$), filtered and concentrated. Flash chromatography over silica gel gave 19 g (39.5%) of product upon elution with $CH_2Cl_2$.

Step 3. 3-Nitro-4-phthalimidooxymethylbenzene-sulfonylchloride.

A solution of the aniline derivative from Step 2 (1.03 g, 2.0 mmol) in $CH_2Cl_2$ (25 mL) was cooled in an ice bath and trifluoroacetic acid (3.0 mL) added. The reaction mixture was stirred in the ice bath under a drierite tube for 6 hours and then at 6° overnight. A cold mixture of acetic acid (10 mL) and conc HCl (10 mL) was added and the mixture cooled to −10°. A solution of sodium nitrite (152 mg, 2.2 mmol) in water (1.5 mL) was added over 10 minutes. After addition was complete, the mixture was stirred at −5° to 0° for an additional 15 minutes and added in a stream to a stirred mixture of $SO_2$ (3 g) in acetic acid (10 mL) and $CuCl_2 \cdot 2H_2O$ (0.22 g) in water (1 mL). After stirring at 0° for 1 hour and then at room temperature for 2 hours, the reaction mixture was poured on ice. The precipated tan solid was filtered off, washed with water and dissolved in EtOAc. After drying and filtering solvent was removed under reduced pressure to give 0.76 g (96%) of product.

Step 4. N-[2-(N-tertbutyloxycarbonyl-N-methylamino)ethyl]-N-methyl-3-nitro-4-phthalimidooxymethylbenzenesulfonamide.

A solution of N-methyl-N-[2-(methylamino)ethyl]-tertbutylcarbamate (0.36 g, 1.92 mmol) and N,N-diisopropylethylamine (0.34 mL, 1.92 mmol) in THF (10 mL) was added over 15 minutes to a stirred cooled solution of the sulfonyl chloride from Step 3 (0.76 g, 1.92 mmol) in THF (20 mL). After addition was complete, the reaction mixture was stirred at ice bath temperature for 30 minutes and then at room temperature for 3 hours. Solvents were removed under reduced pressure and the residue partitioned between EtOAc and brine. The EtOAc extract was dried ($Na_2SO_4$), filtered and concentrated. Flash chromatography of the residue over silica gel and elution with $CHCl_3$ gave 1.0 g (95%) of gummy product.

Step 5. 4-Aminoxy-N-[2-(N-tertbutyloxycarbonyl-N-methyllamino)ethyl]-N-methyl-3-nitro-benzenesulfonamide.

A solution of the product from Step 4 (1.0 g, 1.82 mmol) and 55% hydrazine (116 mg, 2.0 mmol) in EtOH (20 mL) was stirred at 80° for 3 hours. After filtering and concentrating, the residue was flash chromatographed over silica gel. Product, 0.35 g (46%), was eluted as a yellow oil upon elution with 1% MeOH—99%$CHCl_3$.

Step 6. N-[2-(N-tertbutyloxycarbonyl-N-methylamino)ethyl]-N-methyl-3-nitro-4-ureidooxymethylbenzenesulfonamide.

A solution of the hydroxyamine of Step 5 (0.35 g, 0.84 mmol) and 85% trimethylsilylisocyanate (0.27 mL, 1.68 mmol) in toluene (15 mL) was stirred at 80° for 18 hours. After cooling, 10% citric acid (15 mL) was added and the mixture stirred at room temperature for 30 minutes. EtOAc was added and the organic extract was washed with brine, dried (Na2SO4), filtered and concentrated. Flash chromatography of the residue over silica gel and elution with 3% MeOH—97% $CHCl_3$ gave 0.15 g (38%) of product. An analytical sample mp 165.0°-165.5°, was obtained upon recrystallization from MeOH-EtOAc-hexane.

Anal. Calcd. for $C_{17}H_{27}N_5O_8S$: C,44.24; H,5.90; N,15.18. Found: C,44.04; H,5.74; N,15.02.

Step 7. N-Methyl-N-(2-methylaminoethyl)-3-nitro-4-(ureidooxymethyl)-benzenesulfonamide Hydrochloride.

A mixture of the BOC-protected amine of Step 6 (70 mg) and EtOAc (15 mL) was cooled in an ice bath and saturated with hydrogen chloride gas for 5 minutes. After stirring at ice bath temperature for 15 minutes and then at room temperature for 60 minutes, solvent was removed under reduced pressure and the residue recrystallized from MeOH-EtOAc-hexane to give 50 mg (83%) of analytically pure product, mp 195°–197°.

Anal. Calcd. for $C_{12}H_{19}N_5O_6S \cdot HCl$: C,36.23; H,5.07; N,17.61. Found, C,36.15; H,5.11; N,17.73.

washed with brine, dried ($Na_2SO_4$), filtered and concentrated under reduced pressure. Flash chromatography of the residue over silica gel and elution with 5% MeOH—95% $CHCl_3$ gives pure sulfonamide.

Step 2. N,N-Bis[2-(2-tetrahydropyranyl)ethyl]-3-nitro-4-phthalimidooxymethylbenzenesulfonamide A solution of N,N-di-(2-hydroxyethyl)-3-nitro-4-phthalimidooxymethylbenzenesulfonamide (1.02 g, 2.19 mmol), 3,4-dihydro-2H-pyran (0.44 mL, 4.8 mmol) and p-toluenesulfonic acid (0.1 g) in $CH_2Cl_2$ (20 mL) is stirred at 20°–25° for 3 days. After washing with a saturated solution of $NaHCO_3$, the organic layer is dried ($Na_2SO_4$), filtered and concentrated. Flash chromatography of the residue over silica gel with $CHCl_3$ gives the protected sulfonamide.

EXAMPLE 2

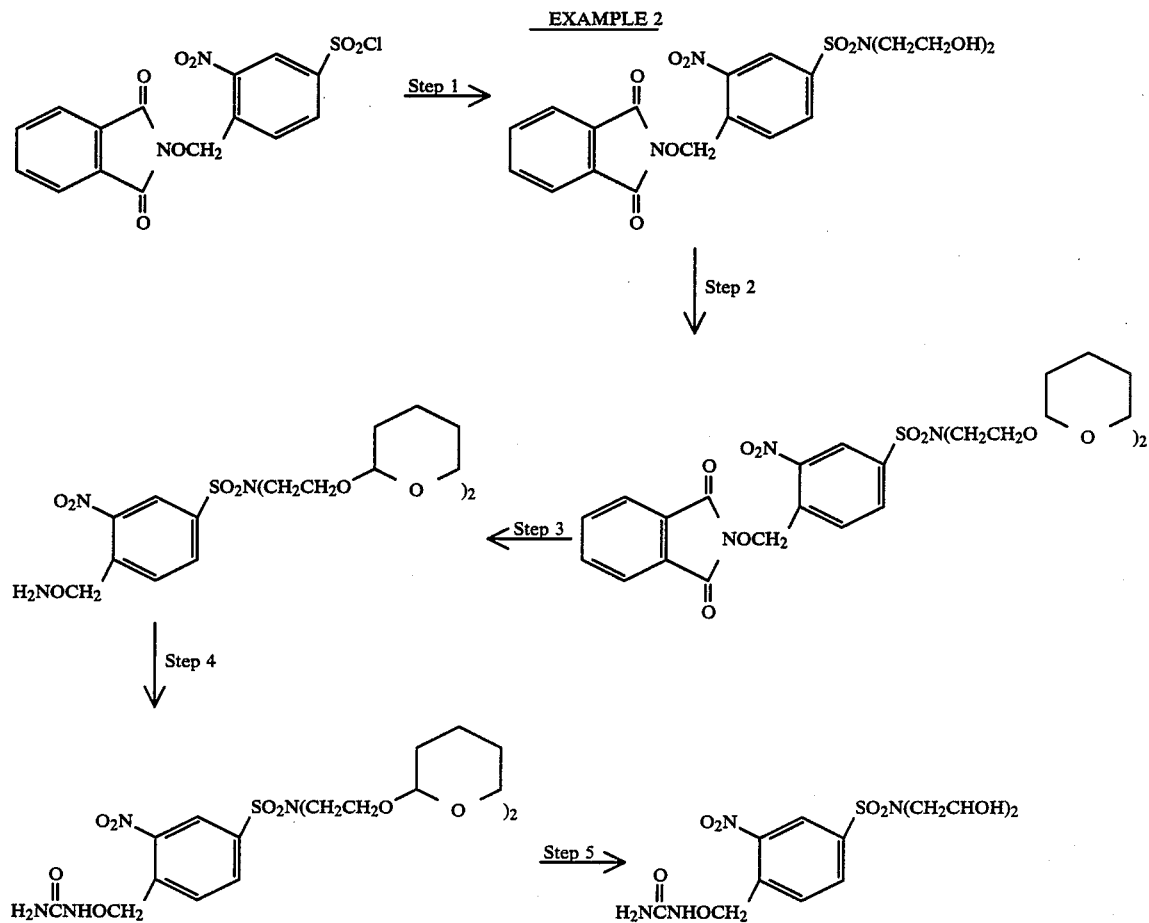

N,N-DI-(2-HYDROXYETHYL)-3-NITRO-4-(UREIDOOXYMETHYL)-BENZENESULFONAMIDE.

Step 1. N,N-Di-(2-hydroxyethyl)-3-nitro-4-phthalimidooxymethylbenzenesulfonamide.

A solution of diethanolamine (0.37 mL, 3.9 mmol) and N,N-diisopropylethylamine (0.68 mL, 3.9 mmol) in tetrahydrofuran (20 mL) is added over 30 minutes to a stirred, cooled solution of 3-nitro-4-phthalimidooxymethylbenzenesulfonylchloride (1.55 g, 3.9 mmol) in tetrahydrofuran (10 mL). After addition is complete, the reaction mixture is stirred in the ice bath for 1 hour, at room temperature for 5 hours, and then is concentrated under reduced pressure. The residue is partitioned between EtOAc and water and the organic extract Step 3. 4-Aminoxy-N,N-bis[2(2-tetrahydropyranyl)ethyl]-3-nitrobenzenesulfonamide.

A solution of the protected sulfonamide of Step 2 (0.95 g, 1.50 mmol) and 55% hydrazine (116 mg, 2.0 mmol) in EtOH (20 mL) is stirred at 80° for 3 hours. After filtering and concentrating, the residue is flash chromatographed over silica gel and product eluted with $CHCl_3$.

Step 4. N,N-Bis[2(2-tetrahydropyranyl)ethyl]-3-nitro-4-ureidooxymethylbenzenesulfonamide.

A solution of the amine of Step 3 (0.40 g, 0.80 mmol) and 85% trimethylsilylisocyanate (0.27 mL, 1.68 mmol) in toluene (15 mL) is stirred at 80° for 18 hours. After cooling, 10% citric acid (15 mL) is added and the mixture stirred at room temperature for 30 minutes. EtOAc is added and the organic extract is washed with brine, dried ($Na_2SO_4$), filtered and concentrated. Flash chromatography of the residue over silica gel and elution with 2% MeOH—98% $CHCl_3$ gives pure product.

Step 5. N,N-Di-(2-hydroxyethyl)-3-nitro-4-(ureidoxymethyl)-benzenesulfonamide.

A solution of the bis tetrahydropyranyl ether of Step 4 (100 mg) in tetrahydrofuran (4 mL), water (2 mL) and glacial acetic acid (6 mL) is stirred at 50° for 20 hours. After concentrating under reduced pressure, the residue is dissolved in EtOAc which is then washed with a saturated solution of $NaHCO_3$ and brine. The EtOAc extract is dried ($Na_2SO_4$), filtered and concentrated and the residue flash chromatographed over silica gel. Elution with 10% MeOH—90% $CHCl_3$ gives pure product.

What is claimed is:

1. A compound having the formula:

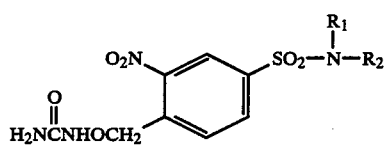

wherein:
$R_1$ is hydrogen, an alkyl group having 1 to 6 carbon atoms, an alkyl group having 1 to 6 carbon atoms in which one or more of the carbon atoms are substituted with a hydroxy group;

$R_2$ is an alkyl group having 1 to 6 carbon atoms in which one or more of the carbon atoms are substituted with a hydroxy group, an alkyl group having 1 to 6 carbon atoms which contains an amino group in which the amino function is substituted with hydrogen or one or two individual alkyl groups having 1 to 6 carbon atoms;

or a pharmaceutically acceptable salt thereof.

2. A compound according to claim 1 which is

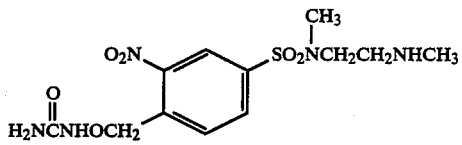

3. A compound according to claim 1 which is

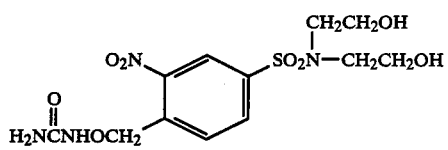

4. A method for enhancing the therapeutic effect of radiation comprising administering to a patient in need of such radiation treatment an effective amount of a compound of claim 1.

5. A pharmaceutical composition for enhancing the therapeutic effect of radiation which consists of an effective amount of a compound of claim 1.

* * * * *